(12) United States Patent
Marin et al.

(10) Patent No.: US 11,589,911 B2
(45) Date of Patent: Feb. 28, 2023

(54) APPLICATION NOZZLE FOR A DEVICE FOR THE DERMO-COSMETIC TREATMENT OF DARK SKIN SPOTS BY CYTO-SELECTIVE CRYOTHERAPY

(71) Applicant: CRYONOVE PHARMA, Chartres (FR)

(72) Inventors: Denis Marin, L'Etang la ville (FR); Jean-Christophe Anton, Strasbourg (FR)

(73) Assignee: CRYONOVE PHARMA, Chartres (FR)

( * ) Notice: Subject to any disclaimer, the term of this patent is extended or adjusted under 35 U.S.C. 154(b) by 282 days.

(21) Appl. No.: 16/958,503

(22) PCT Filed: Dec. 27, 2018

(86) PCT No.: PCT/EP2018/097051
§ 371 (c)(1),
(2) Date: Jun. 26, 2020

(87) PCT Pub. No.: WO2019/129827
PCT Pub. Date: Jul. 4, 2019

(65) Prior Publication Data
US 2021/0059738 A1    Mar. 4, 2021

(30) Foreign Application Priority Data
Dec. 28, 2017 (FR) ...................... 17/71438

(51) Int. Cl.
*A61B 18/02*  (2006.01)
*A61B 18/00*  (2006.01)
*B05B 1/34*  (2006.01)

(52) U.S. Cl.
CPC ........ *A61B 18/0218* (2013.01); *B05B 1/3402* (2018.08); *A61B 2018/0047* (2013.01);
(Continued)

(58) Field of Classification Search
CPC ... A61B 18/0218; B05B 1/3402; B05B 1/005; B05B 1/044; B05B 7/0075
See application file for complete search history.

(56) References Cited

U.S. PATENT DOCUMENTS

| | | |
|---|---|---|
| 2004/0102768 A1 | 5/2004 | Cluzeau et al. |
| 2007/0005048 A1 | 1/2007 | Niedbala et al. |

(Continued)

FOREIGN PATENT DOCUMENTS

| | | | |
|---|---|---|---|
| FR | 2913960 A1 | 9/2008 | |
| WO | WO-9519504 A1 * | 7/1995 | ............. A62C 31/02 |

(Continued)

OTHER PUBLICATIONS

International Search Report (with English Translation) and Written Opinion issued in corresponding International Patent Application No. PCT/EP2018/097051, 10 pages (dated Feb. 11, 2019).

Primary Examiner — Linda C Dvorak
Assistant Examiner — Abigail M Ziegler
(74) Attorney, Agent, or Firm — Buchanan Ingersoll & Rooney PC

(57) ABSTRACT

The disclosure relates to a nozzle for a device for the dermo-cosmetic treatment of dark skin spots by cyto-selective cryotherapy comprising a spray jet supplied by a tank of pressurised liquified cryogenic gas. The nozzle comprises an upper ring for connecting to a shell, extended by a central body of which the side wall which narrows downwards has longitudinal openings and delimits a gas expansion chamber communicating with a frustoconical dispersal conduit arranged inside an end piece to be applied to the skin and opening to the outside through a discharge port.

8 Claims, 5 Drawing Sheets

(52) U.S. Cl.
CPC ............... *A61B 2018/00714* (2013.01); *A61B 2018/00744* (2013.01); *A61B 2018/00916* (2013.01)

(56) References Cited

U.S. PATENT DOCUMENTS

| | | | | |
|---|---|---|---|---|
| 2009/0312693 | A1* | 12/2009 | Thapliyal | A61M 37/0092 |
| | | | | 601/2 |
| 2015/0066005 | A1* | 3/2015 | Fan | A61B 18/0218 |
| | | | | 606/21 |
| 2017/0341093 | A1* | 11/2017 | Hanzlik | B05B 1/005 |
| 2017/0354451 | A1 | 12/2017 | Marin et al. | |
| 2018/0345300 | A1* | 12/2018 | Jurkovic | B05B 1/28 |
| 2019/0000524 | A1* | 1/2019 | Rosen | A61F 7/0085 |

FOREIGN PATENT DOCUMENTS

| | | | | |
|---|---|---|---|---|
| WO | WO-2015185743 | A1 * | 12/2015 | ......... A61B 18/0218 |
| WO | 2016113305 | A1 | 7/2016 | |

* cited by examiner

APPLICATION NOZZLE FOR A DEVICE FOR THE DERMO-COSMETIC TREATMENT OF DARK SKIN SPOTS BY CYTO-SELECTIVE CRYOTHERAPY

CROSS REFERENCE TO RELATED APPLICATIONS

This application is a U.S. National Stage application of International Patent Application No. PCT/EP2018/097051, filed on Dec. 27, 2018, which claims priority to French Patent Application No. FR 1771438, filed on Dec. 28, 2017, the entire contents of both of which are incorporated herein by reference in their entireties for all purposes.

The disclosure relates to an improvement of the device for the dermo-cosmetic treatment of dark skin spots by cyto-selective cryotherapy.

More specifically, the disclosure relates to an improved nozzle intended to be integrated in a device for cosmetic treatment of dark skin spots by cryotherapy as well as the treatment device equipped with said nozzle.

SUMMARY

The treatment device concerned by the disclosure targets, more specifically, the dermo-cosmetic treatment of dark spots situated at the level of the hands, the face, the limbs and the chest area of subjects suffering from such skin hyper-pigmentation.

Such a device is described in WO2016113305 and comprises a tank of pressurised cryogenic fluid, a solenoid valve enabling the discharge of the fluid from the inside of the tank to a spray jet which conveys, via a nozzle, the fluid onto the zone of the skin to treat.

The spray jet comprises at least one axial and cylindrical-conical inner conduit forming a means for limiting the output of cryogenic fluid.

The solenoid valve is associated with an electronic timing system enabling its opening for a predetermined duration.

The transition from the liquid phase to the gas phase, by expansion of the cryogenic fluid, takes place at the level of the nozzle which is intended to produce the desired cryogenic effect while being in contact with the target zone of the skin, that is to say the zone on which is found a dark spot to be removed.

The nozzle is thus one of the essential components of the cosmetic treatment device because it conditions the cryogenic potential of the gas and its impact on the targeted zone of the epidermis and thus directly influences the efficacy of the treatment.

The document US2004/102768A1 describes a cosmetic cryotherapy treatment device comprising, notably, a nozzle provided with an upper ring extended by a central body of which the side wall has, in the lower part, longitudinal openings and delimits an expansion chamber of a cryogenic gas which communicates with a dispersal conduit arranged inside an application end piece and which opens to the outside through a discharge port.

Furthermore, since the dermo-cosmetic treatment involves several successive applications of the cryogenic fluid on the skin, its efficacy depends on the conditions of implementation of the fluid which have to be reproducible in a very precise manner.

More specifically, due to the fact that the cryogenic fluid passes from a liquid phase to a gas phase before arriving at its target, the characteristics of the application nozzle, which is the seat of this transition, are thus important to obtain an optimal temperature curve.

The monitoring of this so-called reference temperature curve makes it possible to create a thermal then osmotic shock impacting the melanocytes while preserving the other cells of the epidermis and the dermis and thus while conserving the cyto-selective character of the dermo-cosmetic treatment.

Qualitatively, this reference temperature curve comprises a rapid decrease in temperature until reaching a stage delimited by a range of temperatures, the maintaining of the temperature in this range of temperatures for a given duration, before undergoing a progressive rise in temperature, until returning to its starting value.

Consequently, the passage of the cryogenic fluid from a liquid phase to a gas phase while following the reference curve is under the influence of several parameters, of which:
  the volume of the gas expansion chamber as well as the relative surface area of its openings communicating with the exterior and thus the profile of the nozzle,
  the distance between the outlet of the spray jet and the target zone of the skin on which the cryogenic effect is going to be applied and thus the height of the nozzle and, in particular, that of the application end piece which is arranged at the outlet of the expansion chamber.

Indeed, the profile of this nozzle turns out to be technically very important because the desired cryogenic effect leads to the formation of crystallised water or frost on the target zone of the epidermis, which makes it possible to maintain a negative temperature stable for a determined duration. Thus, a nozzle of too flat shape would not make it possible to maintain the temperature long enough in the preferential range whereas a too deep shape would lead to a too long contact duration between the target and the crystallised water, leading to too low temperatures.

In these latter conditions, the temperature curve obtained would not correspond to the reference curve.

In parallel, if the height and/or the surface area of the openings of the nozzle are too small, the gas does not have the possibility of expanding and is projected onto the target zone in the form of a mixture of droplets and gas. This liquid phase then accumulates on the target zone, expands progressively and thus leads to uncontrolled and non-reproducible variations in temperature.

In the opposite case, the gas disperses completely in the inner volume of the nozzle and thus cannot bring to the treatment all of its cryogenic potential.

In these two situations, the temperature curve obtained on the zone to treat deviates notably from the reference curve corresponding to an optimal dermo-cosmetic treatment.

The nozzle of the disclosure aims to attain the performance objectives defined above while producing a reproducible and homogeneous cryogenic effect on the zone to treat without modifying the intrinsic cryogenic properties of the gas and thus to enable an efficacious dermo-cosmetic treatment.

This aim is attained according to the disclosure by means of a nozzle, characterised in that it comprises an upper ring for connecting to a shell, extended by a central body of which the side wall which narrows downwards has longitudinal openings and delimits a gas expansion chamber communicating with a frustoconical dispersal conduit arranged inside an end piece to be applied to the skin and opening to the outside through a discharge port.

According to a specific characteristic of the disclosure, the side faces of the longitudinal openings are, in the upper part of the body, flared and turned outwards in a divergent manner and, in the lower part of the body, flared and turned inwards in a divergent manner.

According to a first alternative of the nozzle of the disclosure, the longitudinal openings have sideways side faces.

According to an advantageous characteristic, the height of the frustoconical dispersal conduit and its diameter are, respectively, less than or equal to 10 mm.

This conduit opens to the outside through a discharge port having an axial offset with respect to the axis of the body.

Preferably, this offset is comprised between 1.5 mm and 3.5 mm.

According to another characteristic, the height of the expansion chamber is comprised between 35 and 55 mm.

According to yet another characteristic, the total surface area of the longitudinal slits is comprised between 1080 mm$^2$ and 2160 mm$^2$.

According to a specific alternative embodiment of the nozzle, the section of the central body is substantially trapezoidal and narrows from the top to the bottom.

According to a specific characteristic, the side wall of the body has an inclination of around 8° with respect to the longitudinal axis of the nozzle.

The disclosure also relates to a device for the dermo-cosmetic treatment of dark skin spots comprising a nozzle having the characteristics defined above.

The nozzle of the disclosure makes it possible to obtain a cryogenic effect on the skin which conforms to the reference curve corresponding to an optimal dermo-cosmetic treatment of dark spots.

Thanks to this nozzle, the cryogenic effect is concentrated on a target zone of the skin of small surface area. The device equipped with the nozzle enables the implementation of a particularly efficacious dermo-cosmetic treatment of which the sequences are reproducible in a faithful manner and with great precision of the physical-chemical parameters.

Finally, thanks to this nozzle, the cryogenic effect is distributed homogeneously on the aforementioned target zone of the skin.

BRIEF DESCRIPTION OF THE FIGURES

Other characteristics and advantages of the disclosure will become clear from reading the description that follows, with reference to the appended figures and detailed hereafter.

For greater clarity, identical or similar elements are marked by identical reference signs in all of the figures.

DETAILED DESCRIPTION OF EMBODIMENTS

Naturally, the embodiments illustrated by the figures presented above are only given as non-limiting examples. It is explicitly provided, according to the disclosure, that these different embodiments can be combined with each other to propose others thereof.

Figure 6:
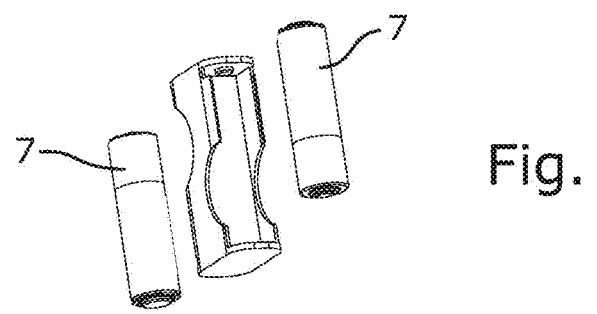
FIG. 6 is an exploded perspective view of the cryotherapy treatment device equipped with the nozzle of the disclosure.
Figure 6:
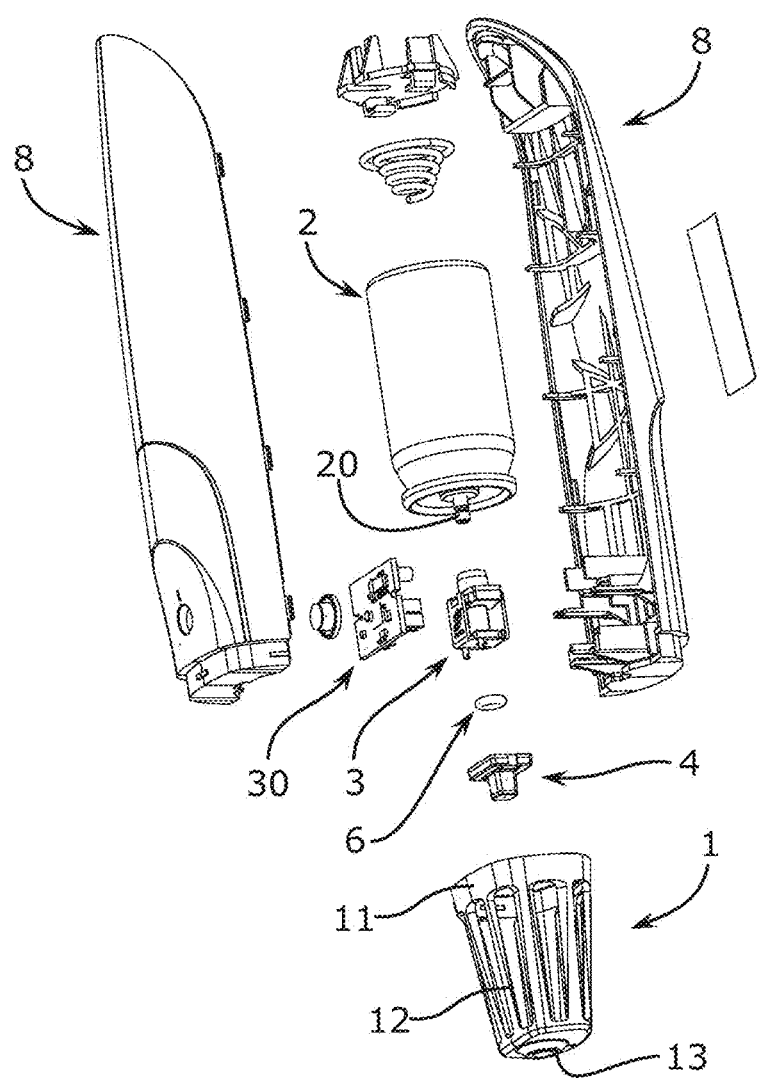

The treatment device, such as represented in FIG. 6, comprises, mainly, a tank 2 of pressurised cryogenic fluid (at around 6 bars), a solenoid valve 3 mounted on the outlet of the tank 2 and driven by an electronic circuit 30, a spray jet 4, a nozzle 1, a seal 6 and a battery 7 (here constituted of two batteries). All of these elements are enclosed in a casing here formed of a shell 8 resulting from the assembly of two half-shells.

The application nozzle 1 is one of the essential components of the device for treating dark spots. It conditions the cryogenic potential of the gas and its impact on the target zone of the skin and thus influences directly the clinical efficacy of the dermo-cosmetic treatment.

The cryogenic fluid is a gas which is in liquid phase and pressurised in the tank 2. The tank 2 is still in open position and is closed off by the solenoid valve 3 mounted directly on its discharge tube 20.

When the solenoid valve 3 passes into open position, the fluid automatically escapes from the tank 2 in the direction of the spray jet 4. The phases of opening and closing of the solenoid valve 3 are driven by the electronic circuit 30 which manages these sequences.

At the outlet of the channel of the spray jet 4, the fluid penetrates into the nozzle 1 where the transition between its liquid phase and its gas phase (expansion of the gas) takes place until reaching the target zone of the skin to produce thereon the desired cryogenic effect.

FIGS. 1, 2A, 2B and 2C represent a preferential embodiment of the nozzle 1 of the disclosure.

This nozzle 1, of longitudinal axis X, comprises an upper ring 11 ensuring its connection and its irreversible fastening to the shell 8. For this purpose, the ring 11 comprises locking members (for example by snap fitting) here in the form of two ports 11a intended to receive complementary pins (not represented) borne by the base of the shell 8.

In the embodiment represented in figures, the ring 11 extends into the lower part by a central body 12 of substantially trapezoidal section of which the side wall 12a is inclined while narrowing downwards with an angle of around 8° with respect to the longitudinal axis of the nozzle 1.

It could be possible however, without going beyond the scope of the disclosure, to produce the body 12 in cylindrical form.

The wall 12a of the body 12, which locally has longitudinal through openings 10, internally delimits a cryogenic gas expansion chamber. The openings 10 ensure, notably, a communication of this chamber with the surrounding external medium which is at ambient temperature and atmospheric pressure.

According to a preferential alternative, the longitudinal openings 10 are constituted of a series of slits, and here 9 slits, each having a height of 40 mm and a width comprised between 6 mm and 7 mm and, preferably, equal to 6.7 mm. These slits are delimited by side edges or faces 10a arranged in the wall 12a of the body 12 and of which the profile is generally bevelled while being sideways over their height.

Figure 1:
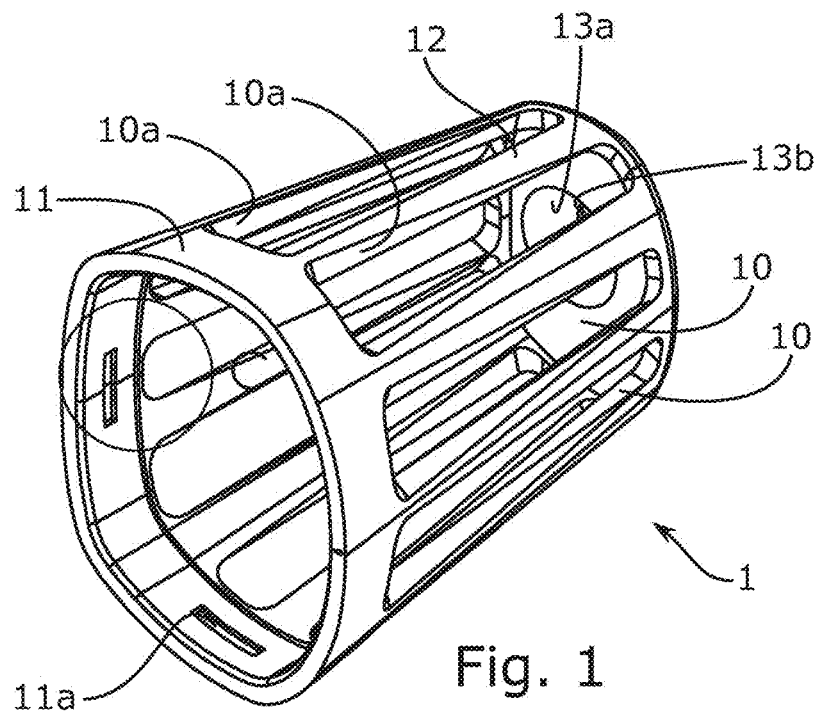
FIG. 1 represents an exploded perspective view of a cryogenic treatment device provided with an embodiment of the nozzle of the disclosure.
Figure 2A:
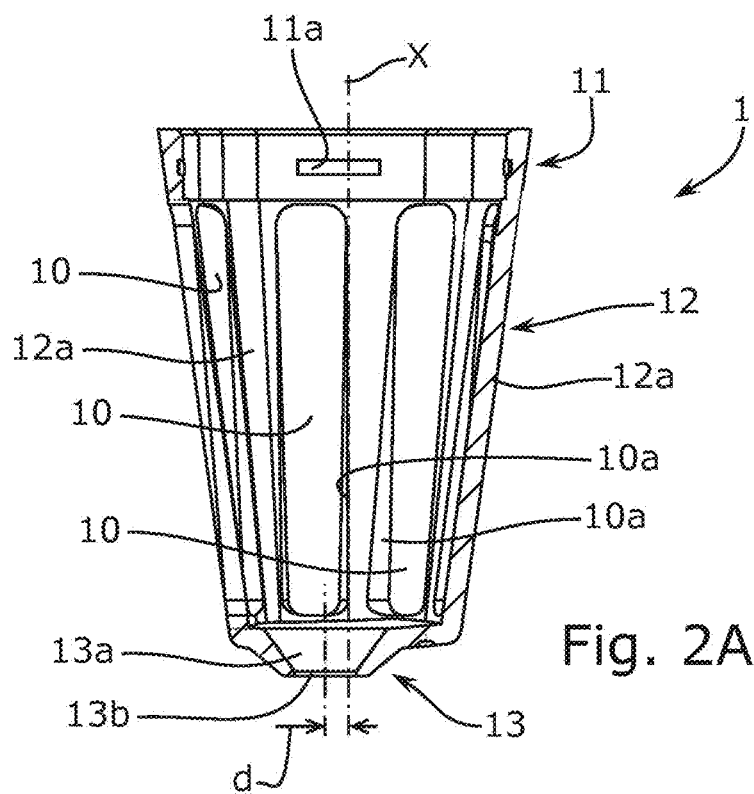
FIGS. 2A, 2B and 2C are, respectively, front, profile and top views of the nozzle of FIG. 1.
Figure 2B:
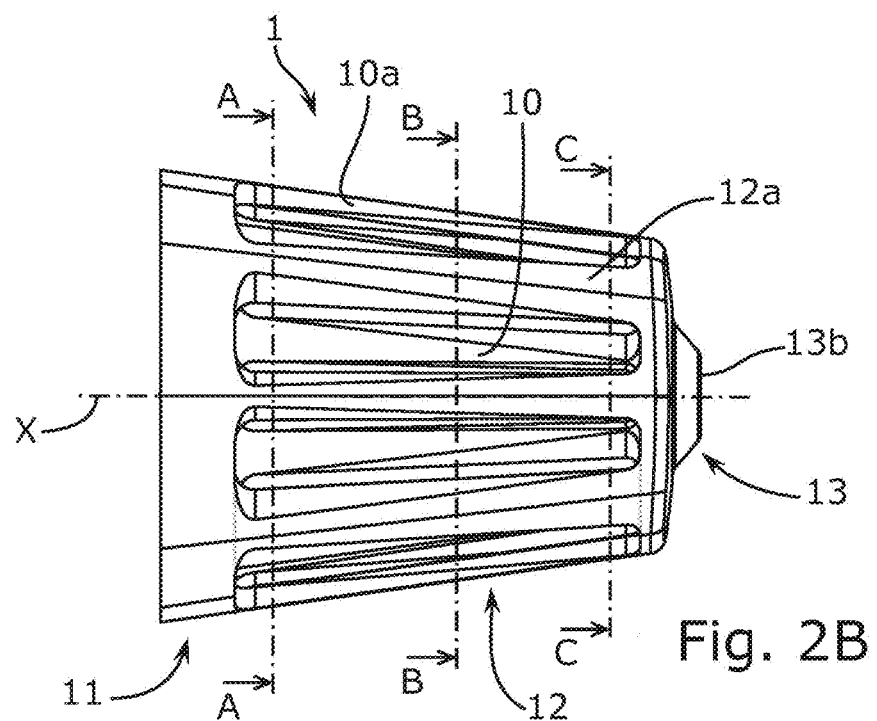
Figure 2C:
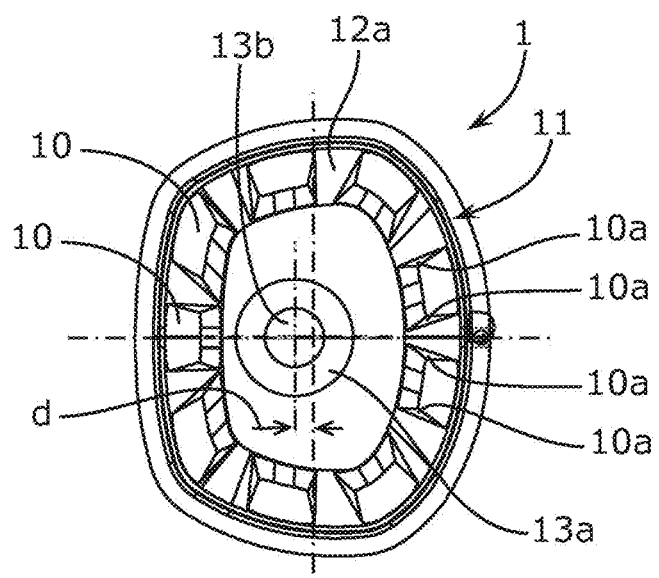
Figure 3A:
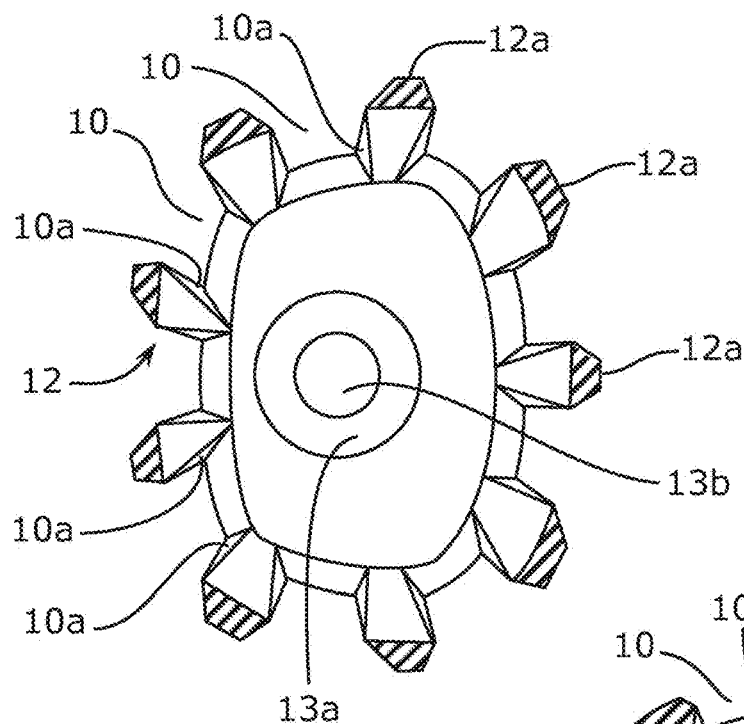
FIGS. 3A, 3B and 3C are sectional views of the body of the nozzle of FIGS. 1 and 2B according to three distinct and parallel planes A, B, C.
Figure 3B:
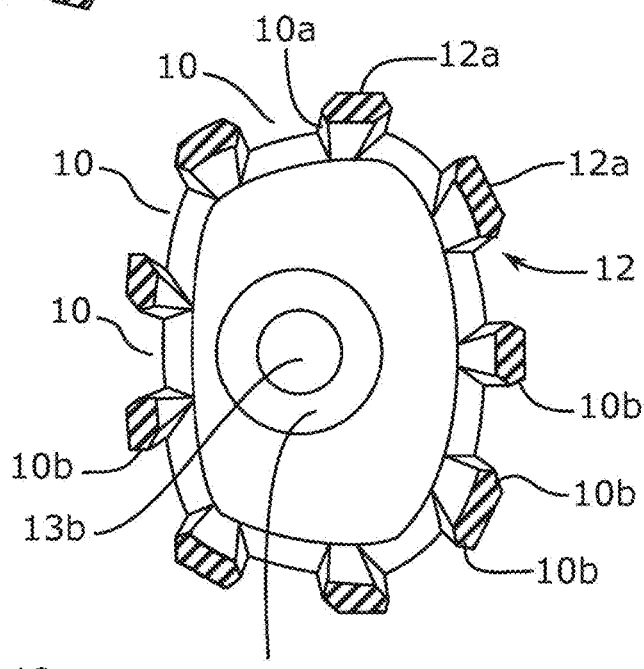
Figure 3C:
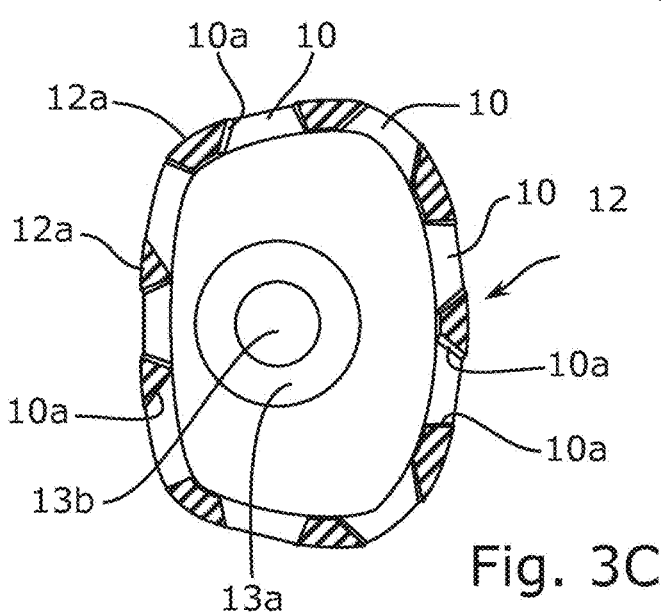

More specifically and as illustrated by FIGS. 2B, 2C and 3A to 3C, on each slit 10, the opposite faces 10a are turned while flaring, on the one hand, outwards in the upper part of the body 12 (FIG. 3A) and, on the other hand, inwards in the lower part (FIG. 3C). The inversion line 10b of the orientation of these faces is situated substantially at mid-height on the slits 10, that is to say at the level of the sectional plane of FIG. 3B where the faces 10a are then locally parallel.

Thanks to this specific profile (of which the functions and the influence on the flow of cryogenic gas will be described in greater detail hereafter), the openings 10 contribute to reinforcing the laminar flow of gas while enabling the gas to expand in a homogeneous manner inside the chamber of the body 12. This expansion brings the gas to atmospheric pressure and thus has an impact on its cryogenic potential and its dermo-cosmetic efficacy. The opening surface area of the body 12, as well as the profile and the geometry of the openings 10, are essential parameters for optimising the cryogenic properties of the gas, as demonstrated hereafter by the tests carried out.

Figure 5:
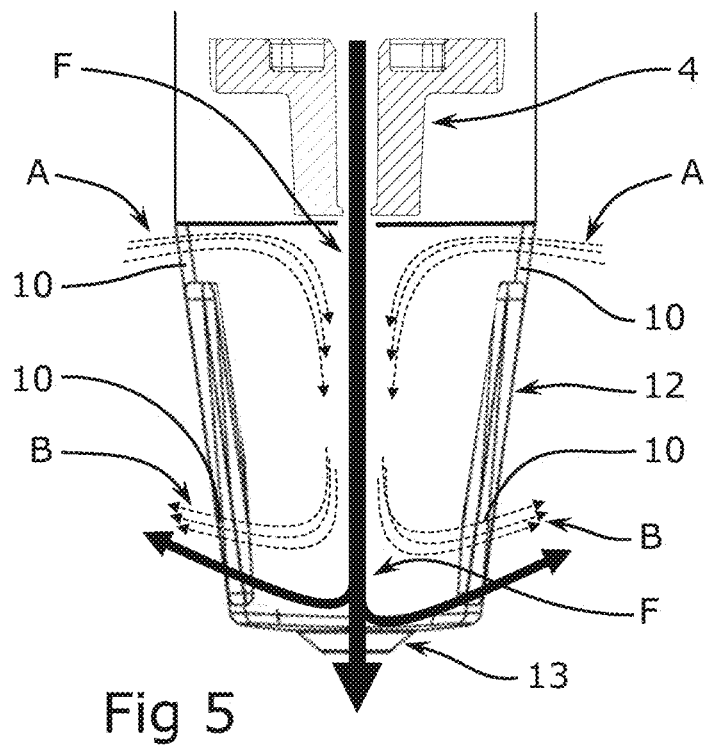
FIG. 5 is a schematic sectional view illustrating the gas flow regime in the nozzle of the disclosure.

Indeed, the gas which is in liquid phase in the tank 2 cannot expand as of the outlet of the solenoid valve 3. This gas thus arrives through the seal 6 in the spray jet 4, while still being in the liquid state. It is only at the outlet of the spray jet 4 that it passes from the liquid phase to the gas phase while undergoing expansion. The pressure along this path then during the transformation of the liquid phase into the gas phase brings about the creation of a laminar flow of gas at the outlet of the spray jet 4, as illustrated by FIG. 5.

The spray jet 4 is constituted of a first channel of 1 mm diameter over a length of 9 mm in its initial part, then a second channel of 0.1 mm length for a diameter of 0.3 mm in its final part. The configuration of the outlet port of the spray jet 4, with walls perpendicular to the axis of the outlet channel, and that of the outlet channel itself, induce a laminar flow F of fluid since the angle of deviation of the flow at the outlet is very low (less than 15°). In addition, the speed of the fluid being determined by its pressure in the tank 2 and the variable diameters of the different components that it passes through, it is relatively low at the outlet of the spray jet 4, which is another characteristic of laminar flow (see FIG. 5).

Obtaining a laminar flow on the target zone is an important objective of the disclosure, yet the gas has to expand in a given volume while establishing a pressure equilibrium with the external air (under atmospheric pressure).

However, this expansion must not interfere with the regimes of laminar flow F coming from the spray jet 4 in order that the gas can arrive with a high homogeneous kinetic and cryogenic potential on its target, that is to say on a zone intended to undergo the dermo-cosmetic treatment. Indeed, if it had to reach its target while being in turbulent regime, the cryogenic effect produced would be neither reproducible, nor homogeneous on the totality of the surface of the zone concerned.

Observing from tests a very high reproducibility of the experimental model as well as homogeneity of the cryogenic effect on the surface of the considered target, the disclosure aims to obtain a stable laminar regime of the gas at the outlet of the end piece 13.

The specific structure of the nozzle 1 of the disclosure allows the gas, at least in the central part of its volume, that is to say in the chamber delimited by the central body 12 (corresponding to a theoretical zone of cylindrical shape of 10 mm diameter), to generate the desired laminar regime.

However, turbulences are observed on either side of the central axis X of the body 12 which are the consequence of two factors. Firstly, the laminar flow F associated with the expansion of the gas has a tendency to push and to displace, in the direction of the end piece 13 and to the outside, at least a part of the volume of air B contained inside the body 12. Jointly, an inverse phenomenon occurs due to the laminar flow F coming from the spray jet 4 and penetrating into the body 12, causes a low pressure in the upper part which brings about a drawing in of external air A to the inside of the nozzle by Venturi effect (FIG. 5).

Yet, the concomitance of these two phenomena of opposite effects is liable to create turbulences and to modify notably the laminar character of the flow of gas inside the nozzle.

More specifically, in the upper part of the body 12, the low pressure resulting in a drawing in of external air A, the laminar regime F is perturbed by the air entering into the chamber of the body 12 via the openings 10.

In addition, in the lower part, the laminar flow F has a tendency to push the volume of occluded air B and is then perturbed by the turbulences that result therefrom, even before its entry into the end piece 13 and its arrival on the target zone.

Consequently, there is a loss of homogeneity and reproducibility of the temperature curves obtained.

It is these phenomena that the disclosure aims to control and to master thanks to the specific profile of the openings 10. Thus, the side faces 10a of the openings 10 form opposite helicoidal ramps and oriented in opposite directions which facilitate the inputs and outputs of air, respectively, in the upper part and in the lower part of the body 12.

The openings 10 of the body 12 favourably influence the regime of the flow of gas and in several ways, all contributing to the same effect, namely, maintaining and reinforcing the laminar flow F of gas up to the target zone while favouring its expansion and while limiting turbulences which could perturb this laminar flow.

With this objective, the disclosure provides that in the upper part of the body 12, the side faces 10a opposite the openings 10 are flared while being turned outwards in a divergent manner to favour the input of air A drawn in by the laminar flow F of gas, as illustrated by FIG. 5.

Conversely, in the lower part of the body 12, the side faces 12a opposite the openings 10 are flared and turned inwards in a divergent manner to facilitate the backflow of air B pushed by the laminar flow F and to ward off turbulences, as also illustrated by FIG. 5.

This configuration further makes it possible to concentrate the cryogenic effect while limiting temperature exchanges (of masses of air) between the inside and the outside of the nozzle.

To summarise, the specific configuration of the openings 10 of the body 12 of the nozzle make it possible to obtain a cryogenic effect that is reproducible and homogeneous on the considered target surface on account of:

- maintaining over a long distance (from the outlet of the spray jet onto the surface of the target zone) a laminar flow;
- limiting the influence of turbulences created on the periphery of this flow by expansion and Venturi effect phenomena;
- concentrating and increasing in power the cryogenic effect at the level of the end piece 13 of the nozzle 1 thanks to the reinforcement of the laminar character of the flow of gas and while avoiding its transition into vortex regime.

As illustrated by the figures, the gas expansion chamber situated inside the body 12 communicates, in its lower part, with a dispersal conduit 13a with frustoconical profile arranged inside an end piece 13, and opening to the outside through a discharge port 13b. The end piece 13 which is situated at the lower end of the nozzle 1 is intended to be applied to the zone of the skin where the dark spot(s) to treat is/are found.

The end piece 13 and, in particular, the discharge port 13b, have an axial offset d with respect to the axis of the body 12 of around 3.80 mm, as illustrated by FIGS. 2A and 2C.

The end piece 13 makes it possible to produce the cryogenic effect on a small surface, while concentrating thereon the cryogenic effect via its central discharge port 13b of which the diameter which is less than or equal to 10 mm and is, preferably, 6 mm (see the tests hereafter), is situated at the outlet of the discharge conduit 13a. The diameter of the port 13b is determined so as to be able to apply the nozzle 1 on the cutaneous zone to treat of which the surface is substantially identical to the section of the port and to concentrate the cryogenic effect in a uniform manner while selectively limiting it to this target zone.

Figure 4:
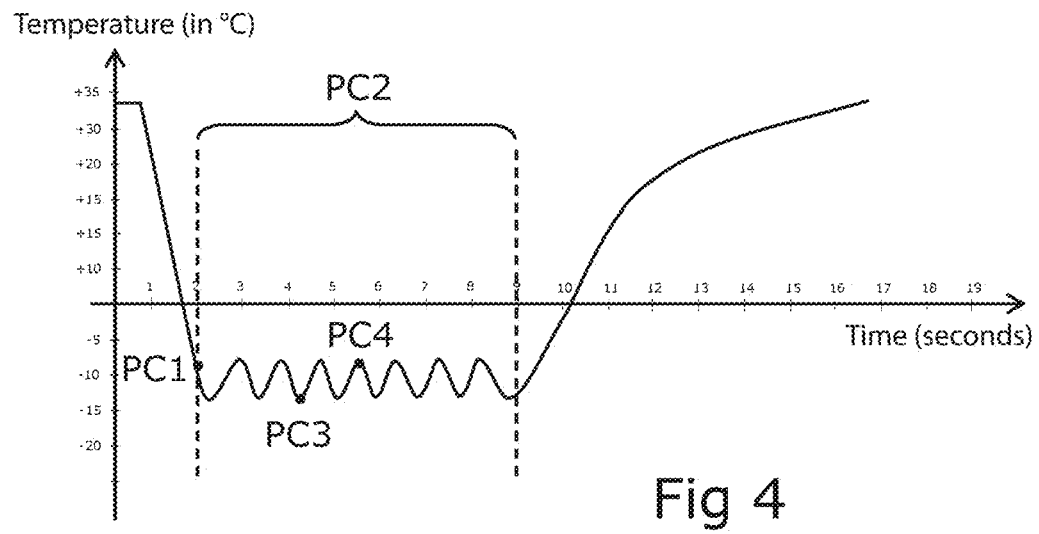
FIG. 4 is a graph representing the reference curve of the temperature of the dermo-cosmetic treatment implemented with the device of the disclosure.

The reference temperature curve illustrated by FIG. 4 represents the variations in the temperature measured at the level of the target zone of the skin per time unit.

Target zone or target is taken to mean the surface on which is positioned the end piece 13 of the nozzle 1 and on which must be applied the cryogenic effect produced by the treatment device. The temperature is measured in degrees Celsius and the durations are measured in seconds. The times are measured from a time noted t0 which corresponds to the moment when the solenoid valve opens to release the pressurised liquid gas. The time t0 also corresponds to the starting of the treatment sequence.

This sequence firstly comprises a rapid decrease in the temperature from the average initial temperature of the epidermis (around 34° C.) for a duration less than 1 second from the opening of the solenoid valve (t0). This drop in temperature makes it possible to reach a stage of negative temperatures where the temperature remains variable by oscillations but is maintained in a range comprised between −15° C. and −5° C. for a duration of at least 7 seconds and at the most 10 seconds. This stage corresponds to the active phase of the dermo-cosmetic treatment of dark spots. The following phase consists in a progressive rise in the temperature up to its starting value.

The parameters of the reference curve, measured at the level of the target zone of the epidermis, are the following (the times are given with respect to t0 corresponding to the opening of the solenoid valve at a moment when the initial temperature of the skin T0 is close to 34° C.):

(PC0) is the origin of the curve at t0 and T0,
(PC1) is the point of the reference curve corresponding to the temperature T1 reached at the time t1 of at the most 2 seconds,
(PC2) is the point of the reference curve at t2; t2-t1 being the duration comprised between 7 and 10 seconds during which the temperature is comprised between −15° C. and −5° C. while being able to vary in this range,
(PC3) is the point corresponding to the temperature threshold (minimum value) recorded on the part of the curve between t1 and t2,
(PC4) is the point corresponding to the temperature ceiling (maximum value) recorded on the part of the curve between t1 and t2,
(PC5) is the point where the temperature of the target zone is 0° C. at t3=10 seconds during the progressive rise in temperature.

This reference curve corresponds to the optimal embodiment of the treatment method which comprises the generation of a thermal then osmotic shock intended to destroy the melanocytes on the target zone of the epidermis and the dermis while preserving the other cells.

This reference curve is obtained and produced in a reproducible and homogeneous manner over the whole of the zone to treat if the gas passes from a liquid phase to a gas phase before arriving on the target zone where it induces the cryogenic effect. The structure of the nozzle 1 conditions the appearance of this phenomenon and is thus critical in this respect. Indeed, the transit of the gaseous flows through the nozzle 1 involves the very critical passage from a liquid phase to a gas phase. Yet, this change of state is influenced by several parameters, of which;

the opening surface area (S) of the openings or slits 10;
the distance (D) between the outlet of the spray jet and the target zone on which the cryogenic effect is intended to be exerted and;
the height (H) of the end piece 13 of the nozzle 1.

Indeed, if the distance (D) and/or the opening surface area (S) of the slits 10 is/are too low, the gas does not have the possibility of expanding and is projected onto the target in the form of an aerosol constituted of a mixture of liquid droplets and gas. The liquid phase thus accumulates on the target, extends outside of the target on zones which must not be treated, expands and evaporates progressively while bringing about uncontrolled variations in temperature, non-reproducible and non-homogeneous over the whole of the zone to treat. In the opposite case, the gas disperses and cannot implement all of its cryogenic potential. In these two situations, the temperature curve obtained does not correspond to the reference curve and the results of the treatment are thus not satisfactory.

Furthermore, in the presence of surrounding residual humidity, the cryogenic effect brings about, on the skin, the formation of crystallised water as ice (frost), which makes it possible to maintain a negative temperature stable for a determined duration.

Yet, a too flat shape of the nozzle 1 (small height) does not make it possible to maintain long enough the temperature in a range comprised between −15° C. and −5° C. whereas a too deep shape (large height H) brings about a too long duration of contact between the target and the crystallised water, then bringing about too low temperatures. The disclosure aims to select a specific profile of the nozzle making it possible to obtain a temperature curve corresponding in a faithful manner to the optimal reference curve.

The experiments and tests carried out and explained hereafter have the objective of verifying and making clear the influence of the different parameters (S), (D) and (H) on the temperature curves obtained at the level of the target zone.

In these experiments, the temperatures are expressed in degrees Celsius and the time in seconds. The figures in bold type in the tables indicate that the values indicated comply with the values or the ranges of values of the reference curve.

The origin of the time (t0) corresponds to the moment when the activation of the electronic circuit 30 starts and, in particular, the control of the solenoid valve 3. For technical reasons, this sequence starts by a rest phase of 0.5 seconds, before the first signal is sent to the solenoid valve 3 to switch it to open position and thus to release the gas from the tank 2.

Indeed, in the treatment device of the disclosure, the tank 2 of gas, maintained in open position, is connected to the solenoid valve 3 which is at rest in closed position. When the solenoid valve 3 is supplied with current via the electronic circuit 30 (programmed sequence), it passes from a closed position to an open position while allowing the gas to escape. The stoppage of the electronic circuit 30 leads to the return to the situation of rest for the solenoid valve 3. A sequence of a series of signals is thus constituted enabling the switching of the solenoid valve to open or closed position according to a very precise order and according to very precise specific durations. The series of switchings of determined durations (and variable from one switching to another), spaced apart according to precise durations correspond to the protocol for clinical implementation of the dermo-cosmetic treatment.

Test 1—Influence of the Height (H) of the End Piece 13 on the Temperature Curve The objective of this test is to carry out different temperature measurements as a function of time while varying the height H of the end piece 13 of the nozzle between 0 and 4.12 mm.

The findings are the following. The height H of the end piece modifies little the shape of the cryogenic curve. On the other hand, the absence of end piece (H=0 mm) does not make it possible to reach temperatures below −15° C. rapidly and the oscillations are not present. On the other hand, for end pieces of height 4.2 mm, 5.6 mm and 6.2 mm, the variations are observed especially in the temperature rise phase but are not however significant.

TABLE 1

Values of the parameters of the reference curve for different heights H of the end piece (0 mm ≤ H ≤ 6.2 mm)

| CRITICAL POINTS | REFERENCES | 4.2 mm | 0 mm | 5.6 mm | 6.2 mm |
|---|---|---|---|---|---|
| PC1 | ≤ −5° C. | −6.56 | −6.88 | −7.01 | −7.18 |
| PC2 | ≥7 sec. | 17.70 | 18.54 | 15.23 | 13.62 |
| PC3 | ≥ −15° C. (+/− 5%) | −14.84 | −14.02 | −15.79 | −16.55 |
| PC4 | ≤ −5° C. (+/− 5%) | −6.55 | −6.88 | −7.01 | −7.16 | fluid to expand in a satisfactory manner. This situation induces perturbations in the measurements made, since there is formation at the level of the target of droplets of fluid (liquid). The temperature curves obtained have oscillations of very important amplitudes then corresponding projections of the liquid. For a given curve, none of the reference values of the parameters is respected (the compliant values being in bold type).

TABLE 2

Values of the parameters of the reference curve for different distances D (25 mm ≤ D ≤ 40 mm).

| CRITICAL POINTS | REFERENCES | 25 mm | 30 mm | 35 mm | 40 mm |
|---|---|---|---|---|---|
| PC1 | ≤ −5° C. | −6.32 | −1.64 | −3.92 | −3.49 |
| PC2 | ≥7 sec. | 4.51 | 8.00 | 10.61 | 10.59 |
| PC3 | ≥ −15° C. (+/− 5%) | −17.75 | −18.64 | −22.72 | −18.43 |
| PC4 | ≤ −5° C. (+/− 5%) | 4.26 | −1.64 | −3.92 | −3.49 |

Important distances (D), in particular, greater than or equal to 45 mm, allow the gas to expand and to exert its cryogenic potential without formation of droplets, with however a drop of this potential as one moves away from the target. For most of the experimental distances, the values of the parameters of the reference curve are not respected (compliant values in green), except for the curves corresponding to the distances D=45 mm and D=55 mm.

TABLE 3

Values of the parameters of the reference curve for different distances D (45 mm ≤ D ≤ 65 mm)

| CRITICAL POINTS | REFERENCES | 45 mm | 50 mm | 55 mm | 60 mm | 65 mm |
|---|---|---|---|---|---|---|
| PC1 | ≤−5° C. | −6.69 | −7.86 | −8.84 | −5.34 | −1.07 |
| PC2 | ≥7 sec. | 13.38 | 10.76 | 8.64 | 5.93 | 0.00 |
| PC3 | ≥−15° C. (+/−5%) | −15.55 | −16.26 | −14.92 | −8.52 | −3.60 |
| PC4 | ≤−5° C. (+/−5%) | −6.64 | −7.86 | −7.24 | −1.61 | 5.42 |

Only the heights 0≥H≥4.2 mm, associated with a specific sequence and with a specific nozzle profile, make it possible to respect the reference values.

By adapting either the sequence, or the shape of the nozzle 1, or the diameter of the channel of the spray jet, it is possible to consider that a range of heights comprised between 0 and 10 mm and, preferably, less than or equal to 6 mm, makes it possible to obtain a cryogenic effect conforming to the values of the reference curve.

Test 2—Influence of the Distance (D) Between the Outlet of the Spray Jet and the Target Zone on the Temperature Curves The objective of this test is to carry out different temperature measurements as a function of time while varying the distance (D) between the outlet of the spray jet and the target between 25 mm and 65 mm.

The findings are the following. Small distances (D) and, in particular, less than 45 mm, to not allow the cryogenic Consequently, only the distances D=45 mm and D=55 mm separating the outlet of the spray jet from the target, associated with a specific spraying sequence and with a specific spray jet, make it possible to respect these values.

Thus, by adapting either the sequence, or the diameter of the channel of the spray jet, it is possible to consider that a range of distances (D) comprised between 35 mm and 55 mm makes it possible to obtain a cryogenic effect conforming to the values of the parameters of the reference curve.

Test 3—Influence of the Opening Surface Area (S) of the Nozzle on the Temperature Curves The objective of this test is to carry out different temperature measurements as a function of time while varying the surface area (S) of the slits 10 of the body 12 of the nozzle 1 and thus by varying, in the horizontal or vertical direction, the exchange surface area with ambient air contributing to the expansion of the gas and to the reinforcement of the laminar flow.

A vertical modification consists in reducing more or less the height of the slits thus decreasing their exchange surface area, compared to a reference nozzle having an overall opening surface area of 2160 mm$^2$, in the outgoing direction of the gas to the target. A horizontal modification consists in reducing more or less the width of the slits, that is to say to close it perpendicularly in the outgoing direction of the gas to the target.

The findings are the following. The body 12 of the nozzle 1 having slits 10 according to the specific configuration of the disclosure and such as illustrated by the figures, makes it possible to obtain a complete expansion of the gas and to use its cryogenic potential to the maximum.

On the other hand, a total closing of the nozzle brings about a curve not conforming to the reference curve, because the expansion of the gas is impossible due to the absence of equilibrium, in a given time, of the pressure of the gas with the surrounding atmospheric pressure.

TABLE 4

Values of the parameters of the curves with a nozzle body without opening (0% opening) and a nozzle body with 9 slits of total opening surface area of 2160 mm$^2$ (100% opening).

| CRITICAL POINTS | REFERENCES | 0 mm$^2$ 0% | 2160 mm$^2$ 100% |
|---|---|---|---|
| PC1 | ≤ −5° C. | −0.91 | −7.26 |
| PC2 | ≥7 sec. | 16.15 | 8.00 |
| PC3 | ≥ −15° C. (+/− 5%) | −13.13 | −7.24 |
| PC4 | ≤ −5° C. (+/− 5%) | 2.82 | −7.18 |

A first observation is that, whatever the sequence, the conformation of the spray jet (thus the output), the quantity of gas administered, the shape of the nozzle and an overall opening surface area of the latter of at least 1080 mm$^2$ enables all of the gas to expand and to have available the totality of its cryogenic potential.

A second observation is that the smaller the percentage opening, the more the curves deviate from the reference curve and the values of its parameters.

TABLE 5

Values of the parameters of the curves for different modes of vertical opening of the slits of the nozzle.

| CRITICAL POINTS | REFERENCES | 2160 mm$^2$ 100% | 1620 mm$^2$ 75% (v) | 1080 mm$^2$ 50% (v) | 540 mm$^2$ 25% (v) |
|---|---|---|---|---|---|
| PC1 | ≤ −5° C. | −7.26 | −6.70 | −6.99 | −1.42 |
| PC2 | ≥7 sec. | 8.00 | 9.58 | 16.50 | 13.73 |
| PC3 | ≥ −15° C. (+/− 5%) | −7.24 | −8.41 | −12.39 | −13.13 |
| PC4 | ≤ −5° C. (+/− 5%) | −7.18 | −6.66 | −6.86 | −0.09 |

TABLE 6

Values of the parameters of the curves for different modes of horizontal opening of the slits of the nozzle.

| CRITICAL POINTS | REFERENCES | 2160 mm$^2$ 100% | 1620 mm$^2$ 75% (h) | 1080 mm$^2$ 50% (h) | 540 mm$^2$ 25% (h) |
|---|---|---|---|---|---|
| PC1 | ≤ −5° C. | −7.26 | −8.43 | −1.86 | −3.10 |
| PC2 | ≥7 sec. | 8.00 | 12.67 | 13.88 | 4.10 |
| PC3 | ≥ −15° C. (+/− 5%) | −7.24 | −8.41 | −12.39 | −13.13 |
| PC4 | ≤ −5° C. (+/− 5%) | −7.18 | −8.41 | −0.41 | −1.64 |

Thus, it may be remarked that the impact on the curves of the opening of the slits of the body of the nozzle is different, for a same percentage, according to whether it is a vertical or horizontal opening.

TABLE 7

Values of the parameters of the curves for a mode of opening to 50% horizontal (noted h) and to 50% vertical (noted v) of the nozzle.

| CRITICAL POINTS | REFERENCES | 2160 mm$^2$ 100% | 1080 mm$^2$ 50% (v) | 1080 mm$^2$ 50% (h) |
|---|---|---|---|---|
| PC1 | ≤ −5° C. | −7.26 | −6.99 | −1.86 |
| PC2 | ≥7 sec. | 8.00 | 16.50 | 13.88 |
| PC3 | ≥ −15° C. (+/−5%) | −7.24 | −12.39 | −12.39 |
| PC4 | ≤ −5° C. (+/−5%) | −7.18 | −6.86 | −0.41 |

The experiment shows that for two identical surfaces (each of 1080 mm$^2$), the temperature curves and their parameters are different according to whether the opening takes place in the vertical or horizontal direction.

By adapting either the sequence, or the diameter of the channel of the spray jet, it is possible to consider that an overall minimum opening of 1080 mm$^2$ is necessary to guarantee a cryogenic effect conforming to that of the reference curve.

The invention claimed is:

1. A nozzle for a device for dermo-cosmetic treatment of dark skin spots by cyto-selective cryotherapy, comprising a spray jet supplied by a tank of pressurized liquefied cryogenic gas, said nozzle comprising an upper ring for connecting to a shell, extended by a central body of which a side wall which narrows downwards has longitudinal openings and delimits a gas expansion chamber communicating with a frustoconical dispersal conduit arranged inside an end piece to be applied to skin and opening to an outside through a discharge port, wherein said discharge port of the end piece has an axial offset with respect to a central axis of the central body, wherein the side wall of the central body has an inclination with respect to a longitudinal axis of the nozzle, wherein said longitudinal openings of the side wall have side faces which are, in an upper part of the central body, flared and turned outwards in a divergent manner, and, in a lower part of the central body, flared and turned inwards in a divergent manner, wherein a section of the central body is substantially trapezoidal and decreasing from the upper part of the central body to the lower part of the central body, and wherein said side faces include sideways side faces.

2. The nozzle according to claim 1, wherein a height of the frustoconical dispersal conduit and a diameter of the frustoconical dispersal conduit are, respectively, less than or equal to 10 mm.

3. The nozzle according to claim 1, wherein the axial offset is between 1.5 mm and 3.5 mm.

4. The nozzle according to claim 1, wherein a height of the expansion chamber is between 35 and 55 mm.

5. The nozzle according to claim 1, wherein a total surface area of the longitudinal openings of the central body is between 1080 mm$^2$ and 2160 mm$^2$.

6. The nozzle according to claim 1, wherein said longitudinal openings of the central body comprise 9 identical slits.

7. The nozzle according to claim 1, wherein the side wall of the central body has an inclination of around 8° with respect to a longitudinal axis of the nozzle.

8. The nozzle according to claim 1, wherein an inner diameter of the nozzle narrows from an inner diameter of the upper ring to the end piece.

\* \* \* \* \*